(12) United States Patent
Barlag et al.

(10) Patent No.: US 8,308,922 B2
(45) Date of Patent: Nov. 13, 2012

(54) ELECTROCHEMICAL TRANSDUCER ARRAY AND USE THEREOF

(75) Inventors: Heike Barlag, Nuremberg (DE); Walter Gumbrecht, Herzogenaurach (DE); Manfred Stanzel, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 886 days.

(21) Appl. No.: 10/587,745

(22) PCT Filed: Jan. 26, 2005

(86) PCT No.: PCT/EP2005/050332
§ 371 (c)(1),
(2), (4) Date: Jun. 23, 2008

(87) PCT Pub. No.: WO2005/073705
PCT Pub. Date: Aug. 11, 2005

(65) Prior Publication Data
US 2008/0283397 A1    Nov. 20, 2008

(30) Foreign Application Priority Data
Jan. 29, 2004  (DE) .................. 10 2004 004 653

(51) Int. Cl.
*G01N 27/26* (2006.01)
(52) U.S. Cl. .............. 204/400; 204/403.03; 204/412
(58) Field of Classification Search .......... 204/600, 204/403.03, 412; 257/730, 737
See application file for complete search history.

(56) References Cited

U.S. PATENT DOCUMENTS

| | | | |
|---|---|---|---|
| 5,635,054 A * | 6/1997 | Girault et al. | ............. 205/775 |
| 6,489,102 B2 | 12/2002 | Corn et al. | |
| 2001/0007373 A1 | 7/2001 | Kadota et al. | |
| 2002/0139981 A1 | 10/2002 | Young | |
| 2002/0195345 A1* | 12/2002 | Bentsen et al. | ............. 204/600 |
| 2003/0017508 A1 | 1/2003 | Charych et al. | |
| 2004/0110230 A1 | 6/2004 | Feldbrugge et al. | |
| 2005/0173246 A1* | 8/2005 | Hodges et al. | ......... 204/403.11 |

FOREIGN PATENT DOCUMENTS

| | | |
|---|---|---|
| DE | 41 31 731 A1 | 5/1993 |
| DE | 44 22 049 C2 | 1/1996 |
| DE | 44 27 921 C2 | 2/1996 |

(Continued)

OTHER PUBLICATIONS

E. Jacobs et al.: "Analytical Evaluation of i-STAT Portable Clinical Analyzer and Use by Nonlaboratory Health-Care Professionals", Clinical Chemistry, 39, 1069 ff. (1993).

(Continued)

*Primary Examiner* — Jeffrey T Barton
*Assistant Examiner* — Steven Rosenwald
(74) *Attorney, Agent, or Firm* — Harness, Dickey & Pierce, P.L.C.

(57) ABSTRACT

Electrochemical transducer arrays are already known from the prior art. According to the invention, the transducer array is provided with at least one flexible, planar metal substrate on which at least one flexible insulator having a firm connection between the metal surface and the insulator surface is disposed. The metal substrate and the insulator disposed thereon are structured in such a manner as to give metal areas which are electrically insulated the one from the other and which serve as sensor areas. The metal substrate used is self-contained so that the structured metal areas can be contacted from the lower side.

28 Claims, 6 Drawing Sheets

FOREIGN PATENT DOCUMENTS

| | | |
|---|---|---|
| DE | 297 17 809 U1 | 4/1998 |
| DE | 199 16 921 A1 | 10/2000 |
| DE | 199 29 264 A1 | 1/2001 |
| DE | 100 09 729 A1 | 9/2001 |
| DE | 100 62 173 C1 | 8/2002 |
| EP | 0 193 251 B1 | 3/1991 |
| EP | 0 504 196 B1 | 8/1995 |
| EP | 1 304 563 A1 | 4/2003 |
| WO | WO 02/02796 A2 | 1/2002 |
| WO | WO 03/043945 A | 5/2003 |
| WO | WO 03/092073 A2 | 11/2003 |
| WO | WO 2004/001404 A1 | 12/2003 |

OTHER PUBLICATIONS

R. Thewes et al.: "Sensor Arrays for Fully Electronic DNA Detection on CMOS", ISSCC Digest of Tech. Papers, 350 ff.

\* cited by examiner

ELECTROCHEMICAL TRANSDUCER ARRAY AND USE THEREOF

This application is the national phase under 35 U.S.C. §371 of PCT International Application No. PCT/EP2005/050332 which has an International filing date of Jan. 26, 2005, which designated the United States of America and which claims priority on German Patent Application number 10 2004 004 653.0 filed Jan. 29, 2004, the entire contents of which are hereby incorporated herein by reference.

FIELD

The invention generally relates to an electrochemical transducer array, and/or to specific uses of a transducer array.

BACKGROUND

Electrochemical transducers are generally subdivided into the three groups of potentiometric, conductometric and amperometric. In the case of potentiometric transducers, the potential is measured with respect to a reference electrode. Ion-selective sensors operate on this basis, and the electrode is in this case coated with an ion-selective membrane. The potential on the electrode is then a measure of the concentration of the corresponding ions. A potentiometric $pCO_2$ sensor can thus also be produced by way of a gas-permeable membrane.

In the case of amperometric transducers, in contrast, a voltage difference is produced between two electrodes, in the case of which the substance to be detected is converted. The currents which flow during the reduction or oxidation process result in the measurement signal. These are widely used as oxygen sensors or biochemical sensors. In the case of a Clark-analogous oxygen sensor, a gas-permeable membrane is applied to the amperometric sensor.

In the case of biochemical sensors, molecular identification systems, such as haptens, antigens or antibodies are placed on or in the vicinity of the electrodes. The target molecule binds thereto and is provided either directly or via intermediate steps with an enzyme label. If the corresponding enzyme substrate is now added, the enzyme releases a substance which can be detected. This is done either optically or electrochemically. This is the so-called ELISA test (Enzyme Linked Immuno Sorbent Assay). DNA analysis methods can also be carried out in a similar way.

The transducers which are used for electrochemical detection must include electrodes with which electrical contact is made individually. During use of potentiometric transducers, the resultant equilibrium potential with respect to a reference electrode must be able to be measured. In the case of amperometric and conductometric transducers, it must be possible to potentiostat the electrodes, and it must be possible to detect the current flow through the electrodes individually.

One example of planar ion-selective sensors is described in E. Jacobs et al, "Analytical Evaluation of i-STAT Portable Clinical Analyzer and Use by Nonlaboratory Health-Care Professionals", Clinical Chemistry, 39, 1069 et seq. (1993). This is a silicon substrate with thin-film electrodes and ion-selective membranes. The sensor electrodes and contacts are in this case located on the same side of the silicon substrate. In order thus to separate the contact surfaces and the flow cell for the analyte, the substrate must be considerably larger than the area which is actually required by the sensors.

Various biochips are likewise manufactured using silicon technology, and are described R. Thewes et al, "Sensor Arrays for Fully Electronic DNA Detection on CMOS", ISSCC Digest of Tech. Papers, 2002, 350 et seq. This has the advantage of the integration of CMOS circuit technology, signal processing (multiplexing) and analog/digital conversion in the sensor platform itself. A large number of sensors can thus be provided in a very small area. One disadvantage relates to the costs for production of a chip such as this and the complex handling (contact-making). The costs per individual sensor are thus high for so-called low-density arrays with fewer than 100 sensors per square centimeter.

Theoretically, it is possible to use polymer mounts with electrodes fitted to the polymer mounts, as an alternative. These can be vapor-deposited or printed on. This method makes it possible to produce individual sensors, for example glucose sensors, at low cost [WO2002/02796-A2]. However, it is not very suitable for arrays since the conductor track structures are coarse, so that the number of electrical contacts is greatly restricted.

Printed circuit board technology is used in the already known eSensor™ from the Motorola Company in order to produce a "low-density" DNA detection system. In this case, both the sensor surfaces and the conductor tracks and contacts are formed on the metallization layer. The product is a rigid printed circuit board with sensors and contacts on the same side. Rear-face contacts can be provided by through-plating. This technique can, however, be implemented only at high cost for large-scale manufacture.

Furthermore, by way of example, so-called microelectrode arrays are known from EP 0 504 196 B1 and DE 297 17 809 U1, in which the sensor cavities have as small an area as possible. DE 199 16 921 A1 discloses a method for production of arrays which are arranged in pairs and are composed of microelectrodes, in which the mount is either silicon or plastic. The aim in this case is to be able to drive the individual electrodes separately. DNA analysis is quoted in particular as an application.

Finally, WO 2004/001404 A1 discloses an array of microelectrodes in which the structure can be varied. The array mounts are in this case glass and/or Captan films, with a single reference-ground electrode being used. Finally, DE 199 29 264 A1 discloses a universal transducer for chemosensors and biosensors, in which a multilayer system is provided with isolating layers and electrode layers, which are used as working, reference-ground and counterelectrodes. The large number of known transducer arrays therefore place particular emphasis on specific microelectrodes, with contact always being made from above.

SUMMARY

In at least one embodiment of the invention, a suitable transducer array is provided which is simple to handle and can be produced at low cost. In at least one additional embodiment, uses of the transducer array are provided.

In the transducer array according to at least one embodiment of the invention, at least one flexible, planar metal substrate is provided, on which at least one flexible isolator is arranged with a permanent connection between the metal surface and the isolator surface. In this case, both the self-supporting metal substrate and the isolator are structured in such a manner that metal surfaces are formed which are electrically isolated from one another and provide the sensor surfaces, in which case the structured metal areas of the self-supporting metal substrate can be contacted from the side facing away from the sensor surface or the side opposite the sensor. This results in a simple measurement capability by way of needle contacts, particularly for decentralized measurement by way of smart cards.

One particularly advantageous feature of at least one embodiment of the invention is the good handling capability of the product. The product is a material composite which is only 100 μm to 200 μm thick and can occupy any desired area. The sensor array is thus highly flexible and, with an appropriate geometry, can be guided on rollers. In the simplest case, the composite comprises a metal layer and an isolator layer. The front face of the metal substrate is covered by the isolator, with only small metal surfaces remaining, which represent the sensors.

Generally, the sensors have to be resistant to aqueous electrolytes and also have to have catalytic activity for the conversion of the chemical substance to be detected. In order to achieve this, they can be coated with noble metals such as platinum, gold or silver. Depending on the requirements of the circuit technology, some areas can be in the form of reference electrodes or counterelectrodes. In particular, it is possible to use a sensor surface coated with silver and chlorided as a reference electrode.

The metal layer can advantageously be used on both sides. The sensors are located, as described, on the front face. The rear face is used to make contact with the sensors. In this case, the metal layer is structured such that each sensor is electrically isolated from the others. The rear-face metal surface which this results in and which corresponds to a single sensor on the front face is considerably larger than the sensor surface. Contact can thus be made at a point which is not located directly underneath a sensor surface and is reinforced by the isolator. Since the metal substrate is self-supporting, the rear-face contact may, however, also be made directly underneath the sensor surface in order in this way to allow a particularly space-saving embodiment. One proposed way to make contact is to use needle cards, which are also used in the application examples.

In the case of a very large sensor array in the form of a strip, it is possible not to make contact with all of the sensors at the same time, but to move in the form of a magazine through the measurement apparatus. The needles would automatically make contact with the sensor surfaces at that time, with the array element being available as an "endless array" for the measurements. This procedure is particularly important for use for automatic monitoring of processes.

Titer plates play an important role in analysis (for example HTS: High Throughput Screening). These contain 96 (8*12), 384 (16*24) or 1536 (32*48) small plastic reaction pots with grid sizes of 9 mm, 4.5 mm and 2.25 mm, respectively. In some cases, optical detection processes can be carried out directly using titer plates such as these. For this purpose, the titer plates have, for example, planar, optically transparent bases. The transducer arrays according to the invention can in this case advantageously be used for electrochemical detection. For this purpose, they are matched to the external dimensions of the titer plates and to the grid side of the small reaction pots. They form the base of the titer plates, so that each small reaction pot has at least one associated electrode. Since contact can be made with the rear face of the transducer arrays according to at least one embodiment of the invention, contact can be made at the same time with all of the electrodes on the titer plate, and they can thus be read at the same time.

A further advantage of the transducer array according to at least one embodiment of the invention, particularly in comparison to silicon-chip technology, is the structure of the array surface. This is not flat. Instead of this, each sensor is located in a depression, which is predetermined by the thickness of the isolator used. These cavities are particularly suitable for accommodation of coatings. They may contain the traps that have been mentioned for DNA analysis, antibodies or selective membranes.

In one specific embodiment, the cavity may even represent a closed electrochemical system. At least one second electrode is required per cavity for this purpose. This can be formed either by division of the sensor surface or by the introduction of a further electrode, which is placed over the cavity as a cover. In this case, this cover is not a fixed component of the sensor array, since the analyte must first be introduced into the cavity. By way of example, it may likewise be joined to the sensor array as a strip. The advantage of a closed arrangement such as this is that the substance to be detected is enclosed in the cavity. It can neither diffuse away, thus attenuating the signal, nor can it reach another sensor where it would result in an incorrect signal.

BRIEF DESCRIPTION OF THE DRAWINGS

Further details and advantages of the invention will become evident from the following description of the figures of example embodiments, on the basis of the drawings in conjunction with the patent claims.

In the figures, in each case illustrated in a schematic simplified form.

DETAILED DESCRIPTION OF THE EXAMPLE EMBODIMENTS

Figure 1:
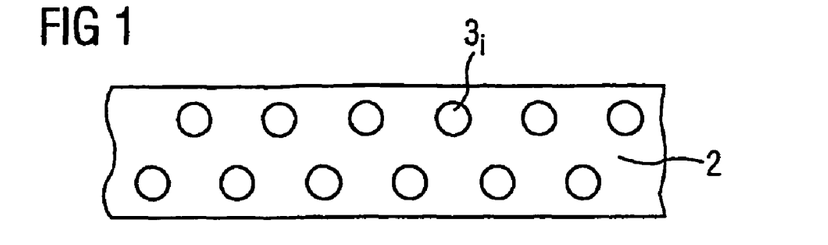
FIG. 1 and FIG. 2 show the front face and rear face of a transducer array.
Figure 2:
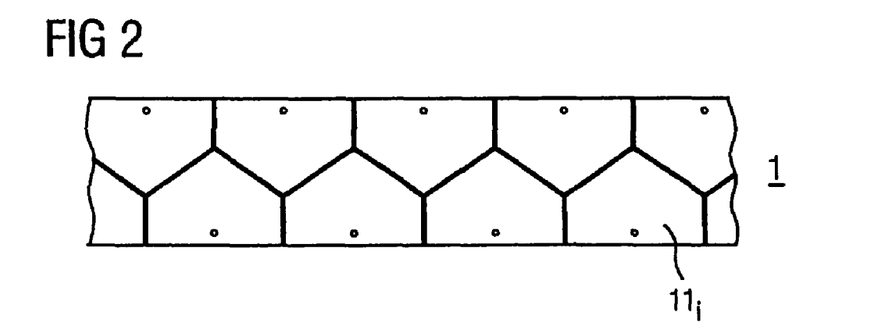

FIGS. 1 and 2 show the front and rear faces of a sensor array comprising a metal substrate 1 and an isolator layer 2. By way of example, circular depressions $3_i$, which are referred to as cavities, are illustrated on the front face. The cavities $3_i$ are produced by the structuring of the isolator 2. The surface of the metal substrate at the bottom of the depressions $3_i$ is exposed.

The illustration of the rear face uses oblique lines to show the subdivision of the metal substrate 1 into parts $10_i$ which are isolated from one another. Each metal island $10_i$ corresponds to the cavity $3_i$ of an isolator cutout on the front face. The possible contact points for a so-called needle card for selectively making electrical contact with the metal surfaces are indicated by dots on the rear face.

Figure 3:
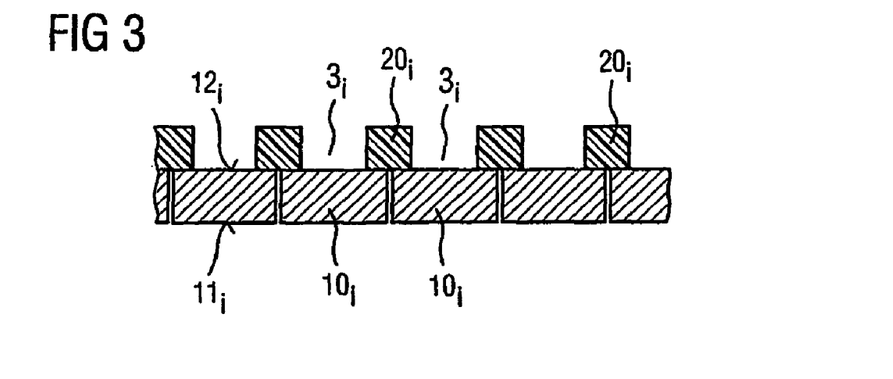
FIG. 3 shows a section illustration of a transducer array as shown in FIGS. 1/2.

FIG. 3 shows a side view of a sensor array, in the form of a section through one row of electrodes or sensors. The separating lines in the metal substrate 1 are illustrated as singular measurement electrodes $10_i$ with a measurement area $12_i$ and an opposite face as a contact-making surface $11_i$. The isolator 2 is located above this, is composed of individual elements $20_i$, holds the self-supporting metal surfaces together, and isolates them from one another.

Figure 4:
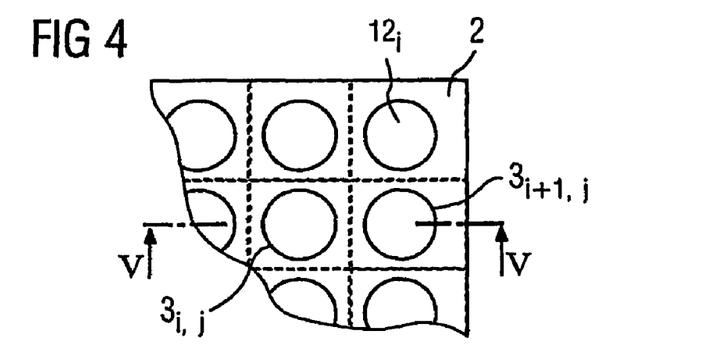
FIG. 4 shows a plan view of a two-dimensional array.

FIG. 4 shows a plan view of a two-dimensional m×n sensor array, in which the cavities $3_i$ and the measurement surfaces $12_i$ are located close to one another. The adjacent cavities $3_i$ and $3_{i+1}$ with measurement surfaces are indicated in the array, in which case the aim is to be able to make contact with the array on the side $11_i$ facing away from or opposite the sensor surface $12_i$. While one sensor is directly adjacent to the other sensors in the area of the m×n array, a side metal area remains free on the rear face of the outer sensor row, for making contact with.

Figure 5:
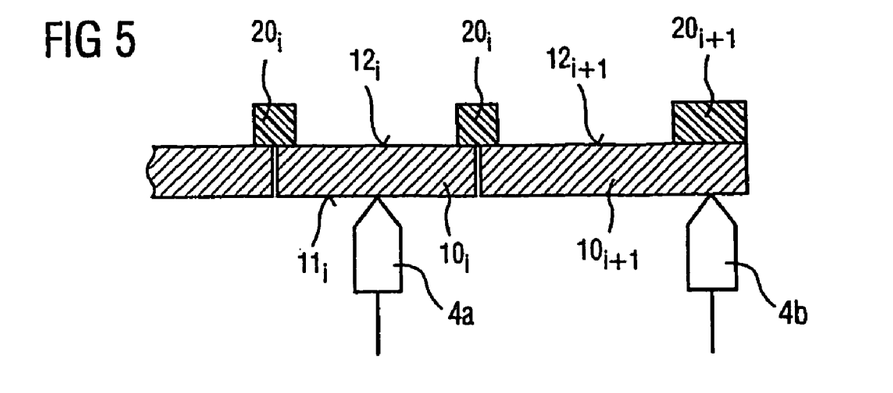
FIG. 5 shows a section illustration, as a partial detail of the transducer array shown in FIG. 4 with the associated contact.

FIG. 5 shows a detail of the sensor array from FIG. 4 with electrodes fitted from the lower face of the metal substrate 1 in order to tap off measurement signals. The measurement technique with the associated measurement apparatus and the electrode arrangement that is advantageously used in this case will be described in detail further below with reference to FIG. 10.

In the case of the first sensor surface, one contact 4a is fitted to the metal surface $11_i$, which is exposed on both sides, centrally, directly opposite the sensor surface. In contrast, in the case of the second sensor surface, contacts 4b may be fitted to the metal surface, which is exposed on one side, laterally offset with respect to the sensor surfaces, since there is sufficient remaining space here.

Figure 6:
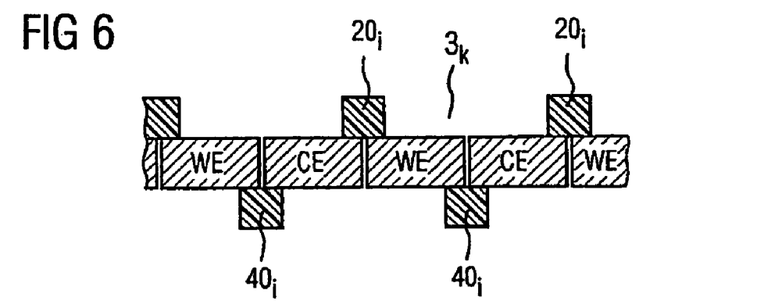
FIGS. 6 to 14 show section illustrations of various variants of a transducer array as shown in FIGS. 1/2.

FIG. 6 shows a sensor array with two electrodes per cavity. For this purpose, the metal substrate is split at this point. The resultant gap is closed by an additional isolator layer $40_i$ from the lower face. In this case, contact surfaces remain free and define measurement electrodes. A working electrode WE and a counterelectrode CE are introduced alternately.

Figure 7:
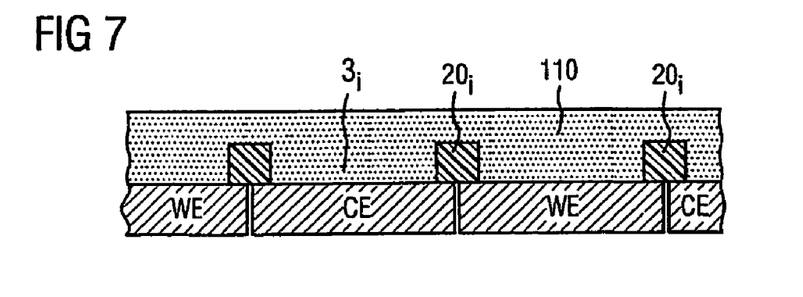

FIG. 7 shows that a plurality of cavities are wetted by the same electrolyte 110. The metal surface of one cavity can then be polarized in the opposite direction to the metal surface of another cavity.

Figure 8:
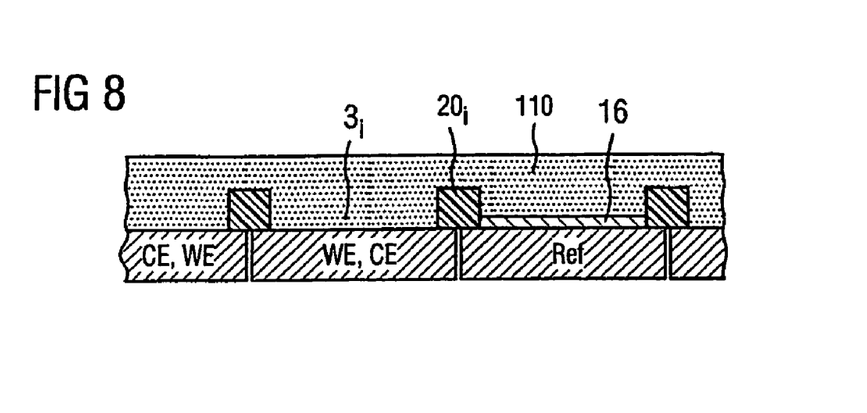

FIG. 8 shows that one of the open metal surfaces is covered on the front face by a thin silver/silver chloride layer 16. This layer $40_1$ can be connected to a potentiostat, together with two further wetted metal surfaces, in a three-electrode arrangement as a working electrode (WE), a counterelectrode (CE) and a reference electrode (Ref).

Figure 9:
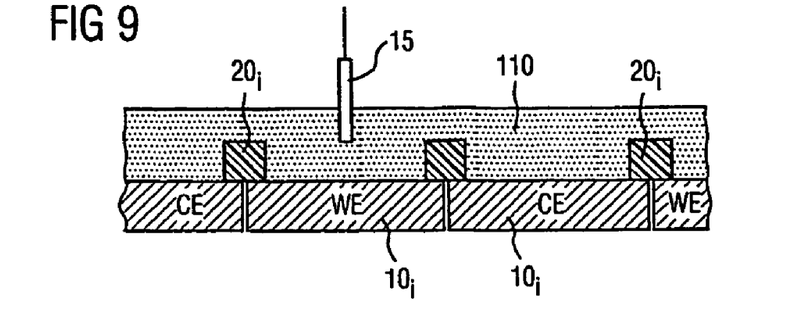

FIG. 9 shows the use of an external reference electrode 15, which is immersed in the common electrolyte which also wets at least two metal surfaces. Together, they can be connected to a potentiostat in a three-electrode arrangement.

Figure 10:
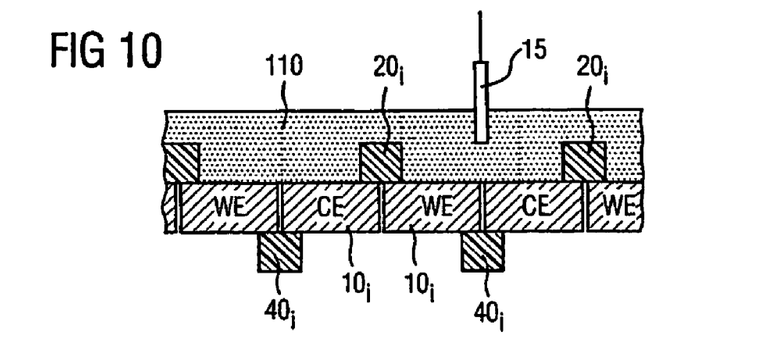

FIG. 10 shows an external reference electrode which is immersed in the same electrolyte as that which also wets a plurality of cavities, each having two electrodes. The two electrodes together with the reference electrode in each case form a three-electrode arrangement.

Figure 11:
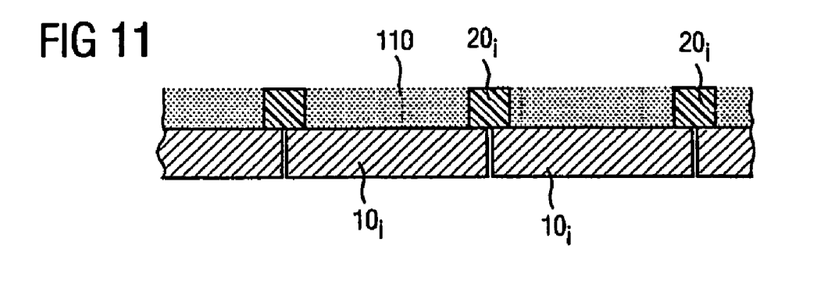

FIG. 11 shows that the electrolyte areas in each cavity can be electrically isolated from the other electrolyte areas.

Figure 12:
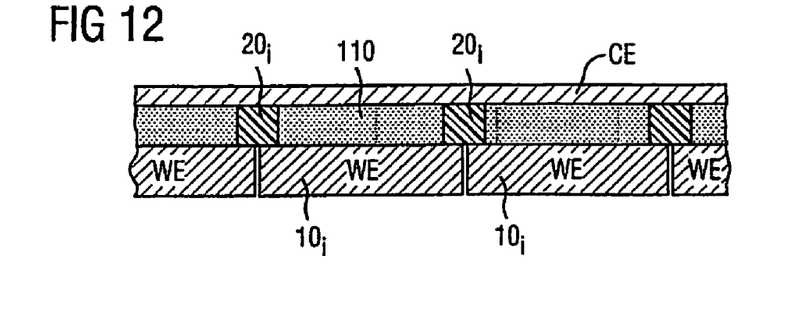

FIG. 12 shows that an electrical conductor which is located above the cavities can be used as a common counterelectrode CE for all of the cavities. A voltage is in each case applied between the metal surface in the cavity and the common counterelectrode.

Figure 13:
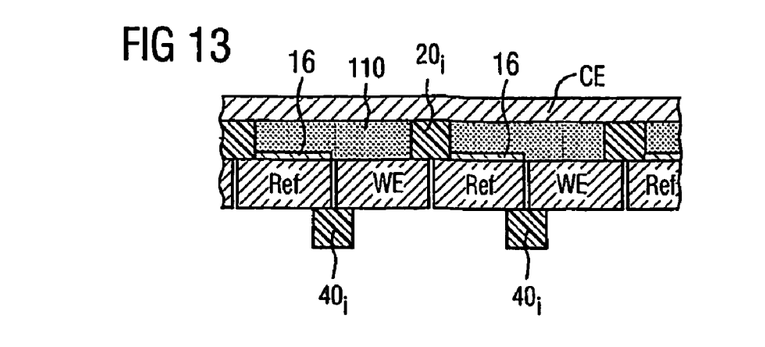

FIG. 13 shows that, in the case of a sensor array with two electrodes per cavity $3_i$ and $3_j$, one of the two electrodes is coated with silver/silver chloride (Ag/AgCl) 16. This coated electrode is connected as a reference electrode to a potentiostat, together with the second electrode in the cavity as the working electrode, and the covering counterelectrode, in a three-electrode arrangement.

Figure 14:
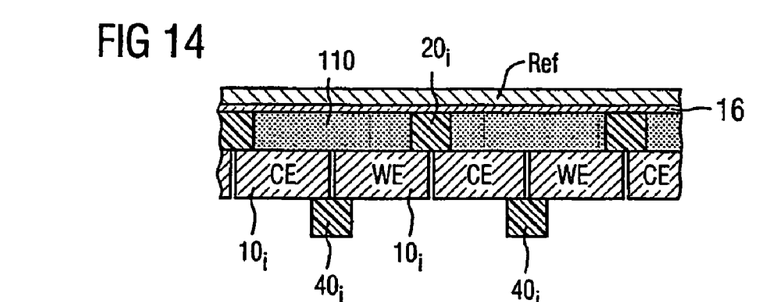

FIG. 14 shows that an electrode which covers the measurement arrangement is coated with silver/silver chloride 16 on the electrolyte side. The sensor array has two electrodes per cavity. A three-electrode arrangement can thus be produced with these two electrodes as the working electrode WE and the counterelectrode CE, and with the covering electrode as the reference electrode.

Figure 15:
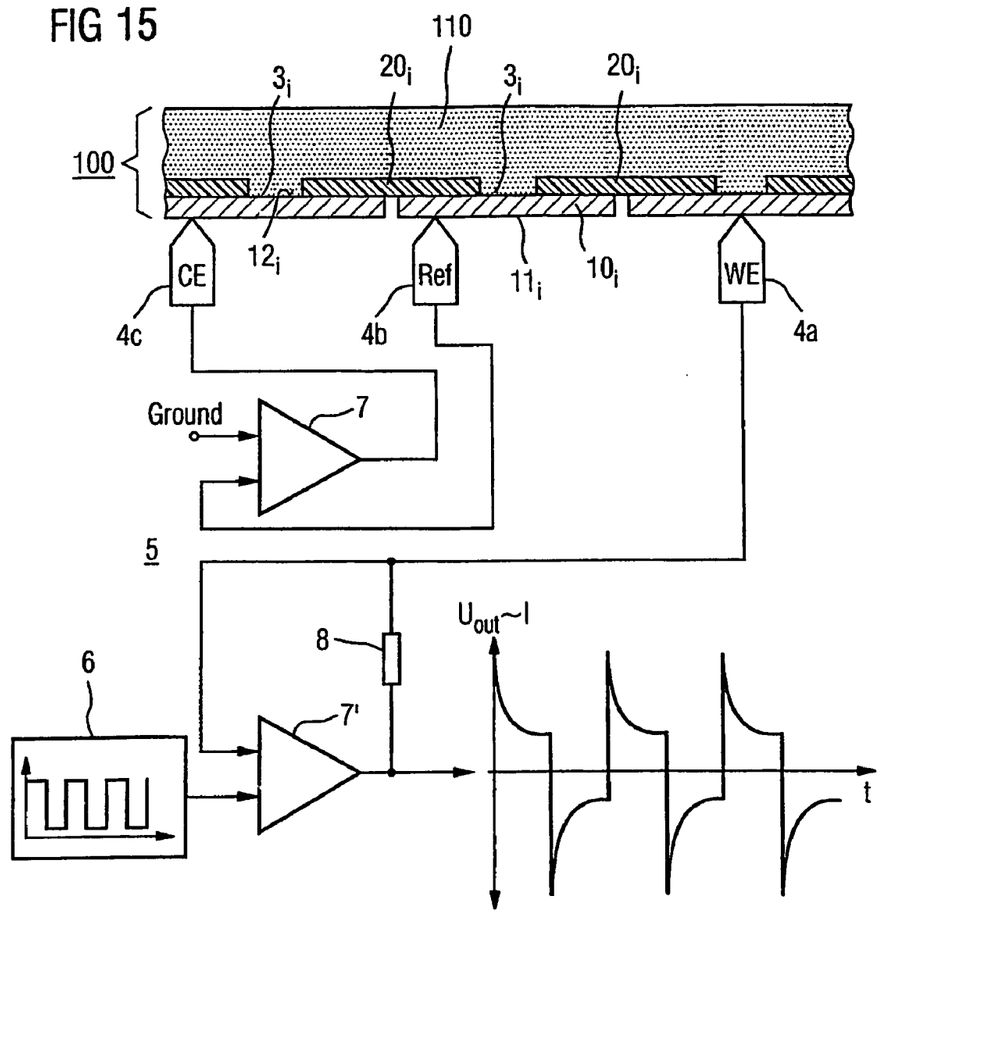
FIG. 15 shows a measurement apparatus using a transducer array as shown in FIGS. 3 to 14.

FIG. 15 illustrates the measurement apparatus in detail. In this case, use can be made of the method of "pulsed" redox cycling, which is described in detail in a parallel application from the same applicant, with the same application priority, and entitled "Method for measurement of the concentration or concentrate change of a redox-active substance, and an associated apparatus".

Apart from being formed by a transducer array 100, various variants of which have been described on the basis of the FIGS. 3 to 14, the measurement layout is essentially provided by a suitable potentiostat 5 in combination with a pulse generator 6, which optionally produces square-wave, triangular-waveform or sinusoidal pulses. The potentiostat 5 is designed in such a manner that suitable potentials are produced, by means of two operational amplifiers 7 and 7', one of which is connected to a "ground" potential, and to one defined measurement resistance. In this case, the pulse duration, the repetition rate and the magnitude of the potential can be predetermined. In particular, the pulse durations of the measurement phases and the relaxation phases can be adjusted separately, and may be of different duration. The potentials may also be of different magnitudes.

The transducer array 100 is associated with the individual electrodes which, by definition, provide a reference electrode RE, a counterelectrode CE and at least one working electrode WE. These electrodes are connected to the potentiostat 5 as a three-electrode arrangement. The signal from the potentiostat 5 is connected to a signal processing unit, which is not illustrated in detail in FIG. 9 but by which an evaluation process is carried out, taking into account the above statements relating to the measurement method and accuracy. In general, this results in $U_{out}$~I for evaluation of the signal profile illustrated in FIG. 15.

In one specific development, a transducer array corresponding to one of the examples described above is used as an ion-selective sensor: a sensor array comprising a metal layer and an isolator layer is used for this example application. The diameter of the cavities is 0.8 mm, the depth is 90 µm, and the distance between two adjacent electrodes is 1 mm. The electrode surfaces are covered with a 2.3 µm thick gold layer. Overall, the array comprises four electrodes, one of which is in the form of a silver chloride reference electrode. The other three electrodes have been coated with an ion-selective membrane. An ammonium-selective membrane is quoted as one example here.

Corresponding to the recommendation of Fluka, the membrane composition was:
  1.00% by weight Ammonium Ionophore I (Fluka 09877)
  33.00% by weight Poly(vinyl chloride) high molecular weight (Fluka 81392)
  66.00% by weight Dibutyl sebacate (Fluka 84838)

A total of 100 mg of the reagents was dissolved in 550 µl of a mixture of cyclohexan and THF, in the ratio 8:2. In each case 35 nl, 45 nl and 60 nl of this solution were spotted into the three sensor cavities, thus resulting in three membranes of different thickness. These were dried for several hours in air.

Figure 16:
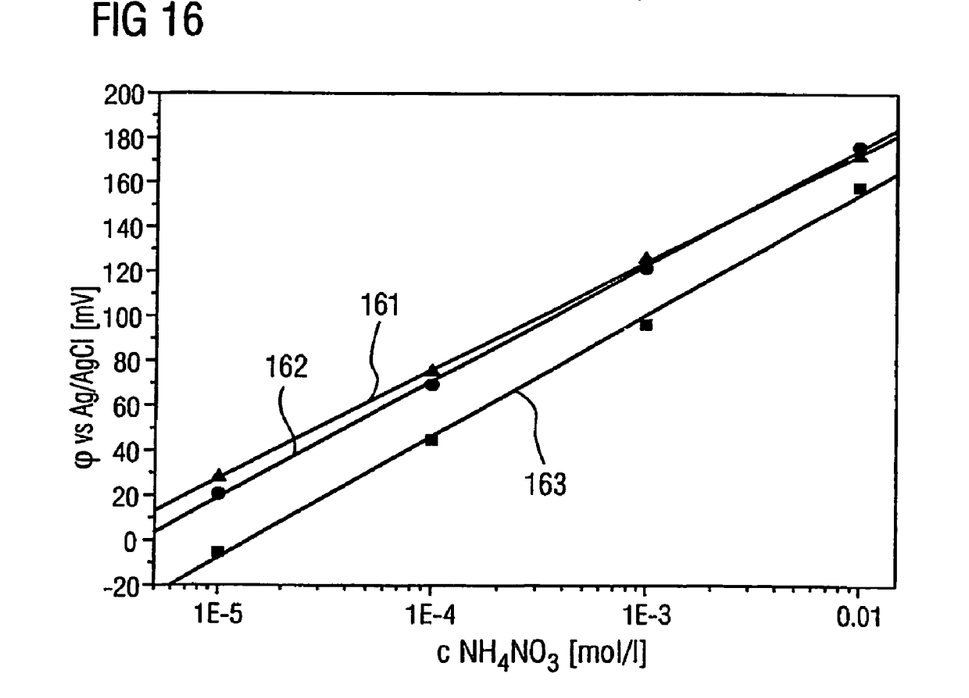
FIG. 16 shows the results of use of a transducer array as an ion-selective sensor.

The sensor array was inserted into a 100 µm deep through-flow channel, and solutions of different $NH_4NO_3$ concentrations were then pumped over it. The solutions also included 100 mM of Tris(hydroxymethyl)aminomethane/hydrochloric acid for buffering at pH 8. The potential difference between the membrane-coated electrodes and the reference-ground electrode was then measured using a high-impedance ohmmeter. The following figure shows the potential change on the sensor as a function of the $NH_4^+$ concentration for the three membrane thicknesses.

FIG. 16 shows the relationship between the potential and the acid concentration. The concentration of $NH_4NO_3$ is plotted on the abscissa in mol/l, and the electrochemical potential φ with respect to an Ag/AgCl electrode is plotted on the ordinate. The graphs 161 to 164 show characteristics for different membranes.

The gradients of the regression lines are 54 mV, 52 mV and 48 mV from the thinnest to the thickest membrane. These values are somewhat less than the theoretical value of 59 mV at room temperature.

In another development, a transducer array corresponding to one of the examples described with reference to FIGS. 3 to 14 is used as a DNA sensor:

The sensor array that is used corresponds to the arrangement that has already been described in the previous example, with four electrode surfaces being used. One of the electrode surfaces is in the form of a reference electrode Ref, another is used as a counterelectrode CE, and the two other electrode surfaces are used as measurement electrodes or so-called working electrodes WE. On one of the working electrodes, a synthetic oligonucleotide sequence of length 25 is anchored on the gold surface by means of a terminal thiol group. The second measurement electrode remains free.

Both surfaces were incubated with a solution of 1 mg of bovine serum albumin per milliliter for 15 minutes, and the sensor array was then inserted into a 100 μm deep throughflow channel. First of all, 10 μl of a 10 μM biotinilated target sequence are pumped over the electrodes within about 5 minutes. After a washing step, a solution of streptavidin-labeled alkaline phosphatase is then passed over it. The washing is carried out using a buffer solution of 100 mM tris (hydroxymethyl)aminomethane titrated to pH 8 with hydrochloric acid, 130 mM NaCl. After washing again, a 2 mM solution of the enzyme substrate paraminophenyl phosphate (pAPP) in the buffer solution is pumped over the sensor array. In the presence of the enzyme alkaline phosphatase, the enzyme substrate pAPP is converted to paraminophenyl (pAP). The pAP is oxidized, with an appropriate potential on the electrode, to form quinonimine. This process can also be reversed, with the quinonimine being reduced to pAP again. In this case:

The reference electrode, counterelectrode and in each case one of the two measurement electrodes are located in a three-electrode arrangement connected to a potentiostat. Owing to the large electrode areas, a potentiostatic measurement method would lead to major depletion of the pAP. A suitable pulsed process is therefore used.

At the start of the measurement, the positive sample, that is to say the electrode with the trap sequence, is connected. The solution with the enzyme substrate first of all flows over the negative sample, then over the positive sample. The flowing movement flushes pAP formed from the enzyme away from the electrodes, so that the current is constant and low when the pump is switched on. If the pump is now stopped, the pAP concentration rises with time because of the enzyme activity. This is evident in the measurement by a major rise in the current signal at 20 nA/s. If the pump is switched on again, then the signal falls to the original value again. This process can be repeated as often as desired.

Figure 17:
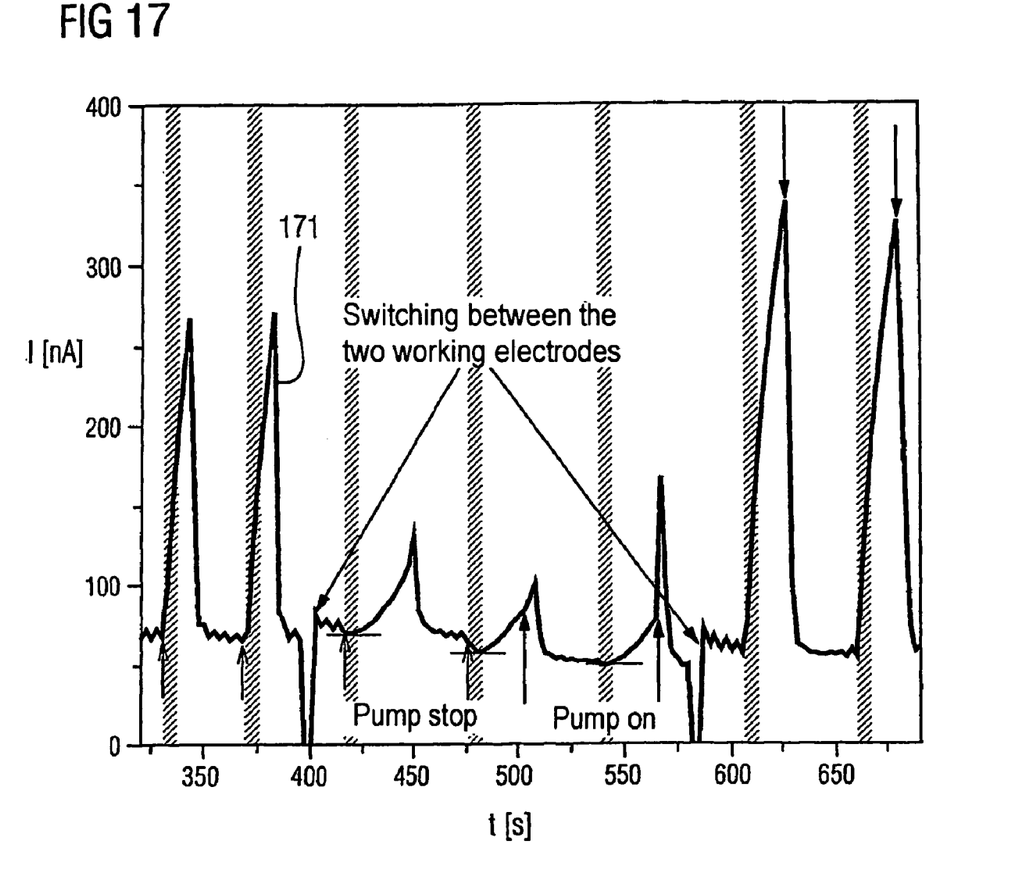
FIG. 17 shows results of the use of a transducer array corresponding to one of FIGS. 1 to 14 as a DNA sensor.

FIG. 17 shows the profile of the measurement current with the pump "on"/"stop" at the sensor with a positive and negative sample. The graph shows the time t in s on the abscissa, and the current I in nA on the ordinate. The graph 171 shows the measurement current in the profile during an experimental investigation.

The negative sample was switched over at t=400 s. Here, the current first of all falls when the pump is stopped, then remains constant for a short time, and then rises slowly. This rise is caused by the diffusion of pAP from the positive sample to the negative sample. When the pump is on, a peak current is added, since the electrolyte first of all flows from the positive sample to the negative sample, and thus transports an increased pAP concentration to the adjacent electrode. Overall, this results in very good discrimination of the positive and negative sample.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A biosensor operating on an electrochemical detection principle, comprising:
    a transducer array, containing a flexible metal/isolator composite composed of a metal layer having a top surface and a bottom surface that separates a first isolator layer from a second isolator layer, with a permanent connection between the top surface of the metal layer and the bottom surface of the first isolator layer and a permanent connection between the bottom surface of the metal layer and the top surface of the second isolator layer and a permanent connection between the bottom surface of the metal layer and the top surface of the second isolator layer,
    the metal layer structured such that individual measurement electrodes and at least one reference electrode are electrically isolated from one another are formed,
    said bottom surface of the first isolator layer, directly contacting said top surface of the metal layer, the first isolator layer having open spaces formed therein such that the top surface of the metal layer has exposed areas as sensor surfaces in the isolator layer;
    said top surface of the second isolator layer directly contacting said bottom surface of the metal layer, the second isolator layer exposing portions of said metal layer such that they can each be electrically contacted with discrete electrodes.

2. The electrochemical biosensor as claimed in claim 1, wherein spaces in the first isolator layer form cavities in which the sensor surfaces are located.

3. The electrochemical biosensor as claimed in claim 1, wherein electrical contacts are provided, with the contacts and the sensor surfaces being located on opposite sides of the metal/isolator composite.

4. The electrochemical biosensor as claimed in claim 3, wherein the contacts are fitted to the metal areas, which are exposed on both sides, directly opposite the sensor surfaces.

5. The electrochemical biosensor as claimed in claim 3, wherein the contacts are fitted to the metal areas, which are exposed on one side, such that the contacts are laterally offset with respect to the sensor surfaces.

6. The electrochemical biosensor as claimed in claim 1, wherein a single sensor surface contains at least two electrically isolated metal areas.

7. The electrochemical biosensor as claimed in claim 6, wherein gaps which form additional isolator areas are formed between the two metal areas on the bottom surface.

8. The electrochemical biosensor as claimed in claim 7, wherein the additional isolator areas leave metal areas free for electrical contact to be made.

9. The electrochemical biosensor as claimed in claim 1, wherein the sensor surfaces are composed of at least one of a noble metal and a noble metal alloy.

10. The electrochemical biosensor as claimed in claim 1, wherein the sensor surfaces are coated with at least one of a noble metal and a noble metal alloy.

11. The electrochemical biosensor as claimed in claim 1, wherein at least one of the sensor surfaces is coated with silver/silver chloride.

12. The electrochemical biosensor as claimed in claim 1, wherein an electrolyte is provided and wets a plurality of sensor surfaces.

13. The electrochemical biosensor as claimed in claim 1, wherein at least two sensor surfaces have voltage appliable to them.

14. The electrochemical biosensor as claimed in claim 1, wherein at least two sensor surfaces, and one sensor surface coated with silver chloride, are connectable as a three-electrode arrangement to a potentiostat, with the sensor surface coated with silver chloride being the reference electrode.

15. The electrochemical biosensor as claimed in claim 1, wherein a separate reference electrode is provided, and is immersed in an electrolyte.

16. The electrochemical biosensor as claimed in claim 15, wherein at least two sensor surfaces and the separate reference electrode are connectable to a potentiostat.

17. The electrochemical biosensor as claimed in claim 15, wherein the electrically isolated metal areas with sensor surfaces have voltage appliable to them.

18. The electrochemical biosensor as claimed in claim 15, wherein the electrically isolated metal areas of one sensor surface and the reference electrode are connectable as a three-electrode arrangement to a potentiostat.

19. The electrochemical biosensor as claimed in claim 2, wherein the cavities contain biochemical identification layers.

20. The electrochemical biosensor as claimed in claim 1, wherein the open spaces on the first surface of the metal substrate form electrolyte areas in individual cavities that are isolated from one another.

21. The electrochemical biosensor as claimed in claim 20, wherein a separate metal surface on the first isolator layer closes the cavities.

22. The electrochemical biosensor as claimed in claim 1, wherein the sensor surfaces have a voltage appliable to them with respect to the additional metal surface.

23. The electrochemical biosensor as claimed in claim 1, wherein one additional sensor surface is provided per cavity and is used as a reference electrode.

24. The electrochemical biosensor as claimed in claim 21, wherein the metal surface which closes the cavities is coated with silver chloride and is used as a reference electrode.

25. The electrochemical biosensor as claimed in claim 1, wherein the sensor surfaces have catalytic activity.

26. The electrochemical biosensor as claimed in claim 1, wherein the first surface of the metal layer in the open spaces of the first isolator layer is exposed.

27. The electrochemical biosensor as claimed in claim 1, wherein the metal layer is exposed on each of the first surface and the second surface at the sensor surface and the bottom surface.

28. The electrochemical biosensor as claimed in claim 1, wherein the metal areas are substantially of the same size and shape.

* * * * *